US00PP29599P2

(12) United States Plant Patent
Hansen

(10) Patent No.: US PP29,599 P2
(45) Date of Patent: Aug. 14, 2018

(54) **X *MANGAVE* PLANT NAMED 'TOOTH FAIRY'**

(50) Latin Name: ***x Mangave* times *Agave***
Varietal Denomination: Tooth Fairy

(71) Applicant: Hans A. Hansen, Zeeland, MI (US)

(72) Inventor: Hans A. Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 15/732,108

(22) Filed: Sep. 19, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para

(57) ABSTRACT

A new and unique X *Mangave* plant named 'Tooth Fairy' characterized by a compact mound of thick, lanceolate, glaucous foliage. Marginal and apical spines long and slightly flexible changing colors from yellow to orange and cinnamon brown with maturity. Teeth and spines leave impression on upper and lower leaves. The new plants is suitable for the garden landscape or as a potted plant in the garden or around the home.

1 Drawing Sheet

Botanical classification: intergeneric hybrid; x *Mangave* times *Agave*.

Variety denomination: 'Tooth Fairy'.

BACKGROUND OF THE INVENTION

The present invention relates to the new and distinct X *Mangave* hybrid plant, X *Mangave* 'Tooth Fairy' hybridized by the inventor at a wholesale perennial nursery in Zeeland, Mich., USA as cross between a proprietary unreleased non-patented X *Mangave* 'Bloodspot' (not patented) as the female or seed parent times a selection of *Agave shawii* (not patented) as the male or pollen parent. The cross was performed on the Dec. 15, 2011 and seeds were harvested Apr. 1, 2012 and sown later on Aug. 8, 2012. Through trials at the same nursery the plant was originally assigned the breeder code XMANG-12-7-41. The new plant has been successfully asexually propagated initially by division at the same nursery in Zeeland, Mich. and also by sterile shoot-tip tissue culture. Both methods of asexual propagation systems have been found to produce stable and identical plants that maintain all the unique characteristics of the original plant.

No plants of X *Mangave* 'Tooth Fairy' have been sold, under this or any name, in this country or anywhere in the world, prior to the filing of this application, nor has any disclosure of the new plant been made prior to the filing of this application with the exception of that which was disclosed or sold within one year of the filing of this application, and was either derived directly or indirectly from the inventor.

BRIEF SUMMARY OF THE INVENTION

X *Mangave* 'Tooth Fairy' differs from its parents as well as all other *Manfreda, Agave* and X *Mangave* known to the applicant. Compared with the female parent the habit of the new plant is more compact with more upright foliage, the foliage is shorter and broader, the foliage coloration is more glaucous blue without greyed purple spotting and the foliage has larger and stiffer marginal and apical spines. Compared with the male parent the new plant has more bluish foliage, longer more orange to brown colored marginal and apical spines. The most similar known cultivars are X *Mangave* 'Silver Fox' U.S. Plant patent application Ser. No. 15/732,109 and X *Mangave* 'Catch a Wave' U.S. Plant patent application Ser. No. 15/732,107. Compared with 'Silver Fox' the new plant longer more orange to brown colored marginal and apical spines and lacks the greyed-purple spotting. Compared with 'Catch a Wave' the new plant has shorter, broader, less coarsely sinuate foliage with larger, less flexible and more orange to brown colored marginal and apical spines and the foliage is more glaucous and lacks the greyed-purple spotting.

The new plant, 'Tooth Fairy', is unique from each of the above cultivars and all *Agave*, X *Mangave* and *Manfreda* known to the inventor by the following combined traits:

1. Compact mound of thick, lanceolate foliage with glaucous surfaces;
2. Marginal and apical spines are long and slightly flexible, changing colors as leaves mature;
3. Teeth and spines on leaves leave impression on upper and lower leaves above or below from when tightly compressed in shoot tip;
4. Moderate growth rate.

BRIEF DESCRIPTION OF THE DRAWING

The drawing of x *Mangave* 'Tooth Fairy' demonstrates the overall appearance of a three-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
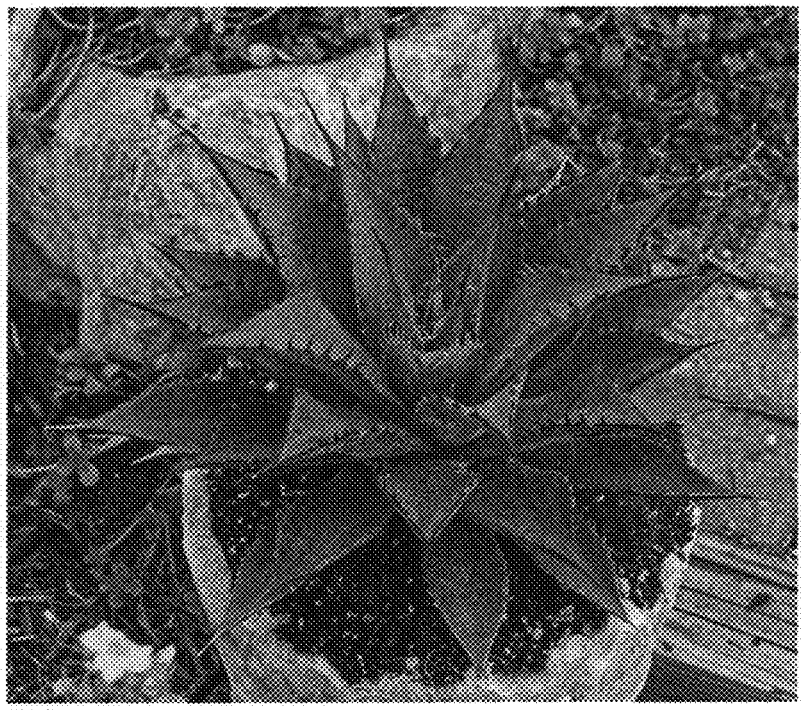
FIG. 1 shows the new plant habit grown in a container.
Figure 2:
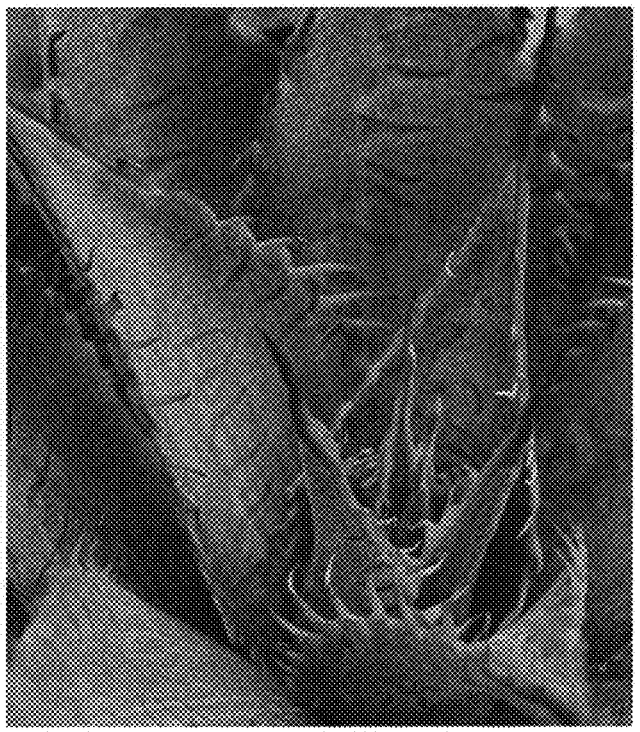
FIG. 2 shows a close-up of the apical and margin spines and also the impression of the spines left on the leaves.

The following descriptions and color references are based on the 2015 edition of The Royal Horticultural Society Colour Chart except where common dictionary terms are used. The new plant, X *Mangave* 'Tooth Fairy', has not been observed under all possible environments. The phenotype may vary slightly with different environmental conditions, such as temperature, light, fertility, moisture and maturity levels, but without any change in the genotype. The following observations and size descriptions are of a three-year-old plant in a commercial wholesale greenhouse in Zeeland, Mich. with supplemental water and fertilizer as needed.

Parentage: X *Mangave* 'Bloodspot' as female (seed) patent and *Agave shawii* as male (pollen) parent;

Propagation: Division of side shoots and sterile shoot-tip tissue culture;

Time to initiate roots from tissue culture: About 21 days;

Growth rate: Moderate;

Crop time: About 14 to 18 weeks to finish in a 3.8 liter container from a 35 mm tissue culture growing at about 21° C.;

Rooting habit: Fleshy, lightly branching, with roots up to 15 cm long;

Root color: Variable depending on grow activity, and soil; between nearest RHS NN155C and RHS 161C;

Plant shape and habit: Succulent, frost-tender, herbaceous perennial with basal rosettes of about 40 thick leaves radially emerging outwardly and upwardly from central stem, producing a radially-symmetrical, rounded mound;

Plant size: Foliage height about 30.0 cm tall from soil line to the top of the leaves and 35.5 cm to 43.0 cm wide at the widest point slightly above soil line in container;

Foliage description: Lanceolate; simple; margins dentate with slightly-flexible spines; thick; lightly glaucous abaxial and adaxial; glabrous abaxial and adaxial; teeth about 1.0 mm long and spaced average about 10 mm apart with slightly-flexible, flexuose to curved spines to about 7.0 mm long; apex acute with flexible terminal spine to about 26.5 mm long; truncate sessile base;

Leaf size: To about 16.0 cm long, about 5.7 cm wide approximately two-thirds toward apex; and about 12.0 mm thick at base; average about 14.5 cm long, 4.8 cm wide and 10.0 mm thick;

Foliage fragrance: None observed;

Leaf blade color:

*Adaxial* (*young*).—Blend between RHS 188A and RHS 122A with impression marks from marginal spines nearest RHS 139A; Abaxial (young): blend between RHS 188C and RHS 122A with impression marks from marginal spines nearest RHS N138A.

*Adaxial* (*lower and more mature*).—Blend between RHS 136B and RHS 137D; Abaxial (lower and more mature): nearest RHS N138D.

*Teeth*.—Variable, beginning nearest RHS 162D, transitioning through nearest RHS 163B, RHS 170A and RHS 178A, maturing nearest RHS 200B.

*Apical spines*.—Nearest RHS 178A as maturing and nearest RHS 200B when mature.

Petiole: Leaves sessile;

Veins: Parallel; not distinct abaxial or adaxial;

Flower description: Not yet observed;

Fruit and seed not observed;

Disease resistance: X *Mangave* 'Tooth Fairy' has not been observed to be resistant to diseases beyond that which is normal for X *Mangave, Agave* or *Manfreda*. The new plant is xeromorphic and survives well with minimal water once established. The new plant is hardy to least USDA zone 10. Full extent of winter hardiness has not been tested.

It is claimed:

1. A new and distinct cultivar of ornamental X *Mangave* plant named 'Tooth Fairy' as herein described and illustrated.

* * * * *